United States Patent
Shirai et al.

(10) Patent No.: US 9,851,424 B2
(45) Date of Patent: Dec. 26, 2017

(54) MAGNETIC RESONANCE IMAGING APPARATUS

(71) Applicant: HITACHI, LTD., Tokyo (JP)

(72) Inventors: Toru Shirai, Tokyo (JP); Yoshitaka Bito, Tokyo (JP); Yo Taniguchi, Tokyo (JP); Satoshi Hirata, Tokyo (JP); Yoshihisa Soutome, Tokyo (JP); Tetsuhiko Takahashi, Tokyo (JP); Hiroyuki Itagaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 751 days.

(21) Appl. No.: 14/375,488

(22) PCT Filed: Jan. 10, 2013

(86) PCT No.: PCT/JP2013/050290
§ 371 (c)(1),
(2) Date: Jul. 30, 2014

(87) PCT Pub. No.: WO2013/114927
PCT Pub. Date: Aug. 8, 2013

(65) Prior Publication Data
US 2015/0008925 A1    Jan. 8, 2015

(30) Foreign Application Priority Data

Jan. 30, 2012    (JP) .................. 2012-016781

(51) Int. Cl.
*G01R 33/46* (2006.01)
*G01R 33/56* (2006.01)
(Continued)

(52) U.S. Cl.
CPC .......... *G01R 33/4625* (2013.01); *A61B 5/015* (2013.01); *A61B 5/055* (2013.01);
(Continued)

(58) Field of Classification Search
CPC .... A61B 5/015; A61B 5/055; G01R 33/4804; G01R 33/4625; G01R 33/543; G01R 33/5608; G01R 33/565
(Continued)

(56) References Cited

U.S. PATENT DOCUMENTS

| | | |
|---|---|---|
| 2002/0180438 A1 | 12/2002 | Froundlich et al. |
| 2012/0071746 A1* | 3/2012 | Vortman ............ G01R 33/4804 600/411 |
| 2016/0192859 A1* | 7/2016 | Shirai .................. A61B 5/0042 600/412 |

FOREIGN PATENT DOCUMENTS

| | | |
|---|---|---|
| JP | 11-253420 A | 9/1999 |
| JP | 2004-527351 A | 9/2004 |

(Continued)

OTHER PUBLICATIONS

International Preliminary Report on Patentability from International Application No. PCT/JP2013/050290 dated Aug. 14, 2014.

(Continued)

*Primary Examiner* — Melissa Koval
*Assistant Examiner* — Rishi Patel
(74) *Attorney, Agent, or Firm* — Brundidge & Stanger, P.C.

(57) ABSTRACT

There is provided a technique for obtaining temperature information for inside of a living body and accuracy information thereof in short time with low burden imposed on a subject. It is realized with a spectrum calculator configured to perform MRS or MRSI measurement for two kinds of substances showing difference of resonant frequencies and calculating spectra of magnetic resonance signals of the two kinds of substances, a temperature information calculator configured to calculate temperature information for inside of the subject on the basis of peaks of the calculated spectra, a temperature accuracy information calculator configured to (Continued)

calculate temperature accuracy information indicating accuracy of the temperature information on the basis of peaks of the calculated spectra, and a display information generator configured to generate display information to be displayed on a display device on the basis of the temperature information and the temperature accuracy information.

15 Claims, 13 Drawing Sheets

(51) Int. Cl.
<table>
<tr><td>G01R 33/565</td><td>(2006.01)</td></tr>
<tr><td>G01R 33/54</td><td>(2006.01)</td></tr>
<tr><td>A61B 5/055</td><td>(2006.01)</td></tr>
<tr><td>G01R 33/48</td><td>(2006.01)</td></tr>
<tr><td>A61B 5/01</td><td>(2006.01)</td></tr>
</table>

(52) U.S. Cl.
CPC ....... G01R 33/4804 (2013.01); G01R 33/565 (2013.01); *G01R 33/543* (2013.01); *G01R 33/5608* (2013.01)

(58) Field of Classification Search
USPC .................. 324/309, 315, 318; 600/410–412
See application file for complete search history.

(56) References Cited

FOREIGN PATENT DOCUMENTS

<table>
<tr><td>JP</td><td>2005-304558 A</td><td>11/2005</td></tr>
<tr><td>JP</td><td>2008-086525 A</td><td>4/2008</td></tr>
</table>

OTHER PUBLICATIONS

International Search Report from International Application No. PCT/JP13/050290 dated Feb. 12, 2013.

E. Cady, et al., "The Estimation of Local Brain Temperature by in Vivo H Magnetic Resonance Spectroscopy" Magnetic Resonance Medicine, 1995, vol. 33, P862-867.

J.C. Hindman, The Journal of Chemical Physics, 1966, vol. 44, P4582-4592, "Proton Resonance Shift of Water in the Gas and Liquid States".

* cited by examiner

100

120

130

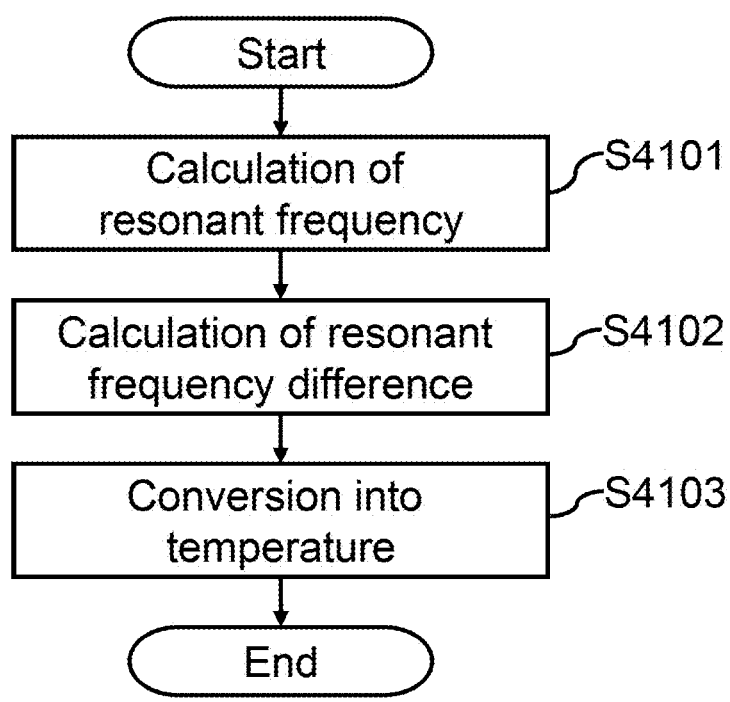

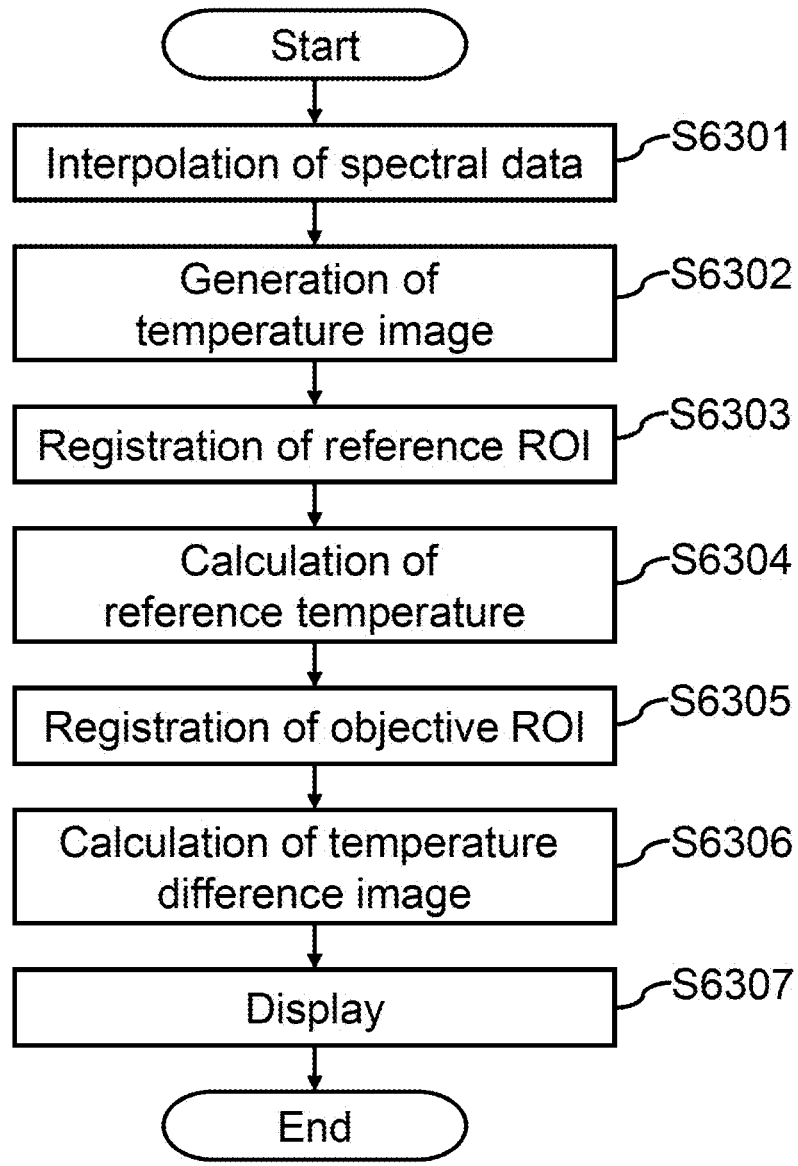

MAGNETIC RESONANCE IMAGING APPARATUS

TECHNICAL FIELD

The present invention relates to a magnetic resonance imaging technique. In particular, the present invention relates to a technique for magnetic resonance spectroscopy (MRS) or magnetic resonance spectroscopic imaging (MRSI), in which a temperature image is calculated from difference of resonant frequencies of water and metabolite.

BACKGROUND ART

Magnetic resonance imaging apparatuses are apparatuses for obtaining physical and chemical information of an object of measurement by irradiating a radio frequency magnetic field of a specific frequency on the object of measurement placed in a static magnetic field to induce magnetic resonance phenomenon. The magnetic resonance imaging (MRI) method currently widely spreading is a method of imaging hydrogen nucleus density, difference of relaxation time, or the like, which differs depending on type of body tissue, by mainly using magnetic resonance phenomenon of protons in water molecules. Difference of tissues can be thereby imaged, and thus it is highly effective for diagnosis of diseases.

On the other hand, MRS and MRSI are methods of separating magnetic resonance signals for every molecule (metabolite) on the basis of difference in resonant frequency thereof (chemical shift) caused by difference of chemical bonds in the molecule, and measuring density, difference of relaxation time, or the like for every molecular species. MRS is a method of observing molecular species in a certain selected special region, and MRSI is a method of imaging every molecular species. The atomic nuclei used as the object include those of $^1$H (proton), $^{31}$P, $^{13}$C, $^{19}$F, and so forth.

Major metabolites existing in human bodies and detectable by proton MRS or proton MRSI utilizing protons as the objective nucleus species (henceforth referred to simply as MRS and MRSI) include choline, creatine, N-acetylaspartate (NAA), lactate, and so forth. It is expected to perform non-invasive stage determination or early diagnosis, and diagnosis of malignancy of metabolic disorders such as cancers, on the basis of amounts of such metabolites.

MRS and MRSI are applicable not only to measurement of metabolite densities, but also to thermometry in living bodies utilizing difference of resonant frequencies of water and metabolite. It is known that the resonant frequency shift of water depends on temperature, and the temperature coefficient of the shift amount is −0.01 ppm/° C. (for example, Non-patent document 1). It is also known that resonant frequencies of such metabolites as NAA do not change in the temperature range under the physiological environment. There is a technique for measuring a temperature in a living body on the basis of the difference of resonant frequencies of water and metabolite utilizing the above characteristics (refer to, for example, Non-patent document 2).

The temperature information is calculated by fitting with a model function, for example, as follows. First, water and metabolite (the following explanation will be made for NAA as an example) are measured individually or simultaneously. Then, the measured data are subjected to the Fourier transform in the time direction to obtain spectra, respectively. Fitting of the measured peak regions (spectral peaks) of water and NAA is performed by using, for example, the Lorenz type function represented by the following equation (1).

[Equation 1]

$$L_i(v) = \frac{a_i^2 I_i}{a_i^2 + 4(v - v_i)^2}\cos\phi_i + \frac{2a_i I_i(v - v_i)}{a_i^2 + 4(v - v_i)^2}\sin\phi_i + c \quad (1)$$

In the equation, $\mu$ represents frequency, $L_i$ represents signal intensity, $v_i$ represents resonant frequency of an objective substance, $a_1$ represents half-hand width of spectral peak, $I_i$ represents height of spectral peak, $\phi_i$ represents phase, and c represents a constant term. Fitting of the measured spectral peaks of water and NAA is performed with the function of the equation (1) to obtain the resonant frequencies of water and NAA, respectively, as resonant frequency $v_i$, which is a fitting parameter. Then, difference of resonant frequencies of water and NAA is calculated, and temperature is calculated in accordance with, for example, the temperature conversion equation described in Non-patent document 2.

PRIOR ART REFERENCES

Non-Patent Documents

Non-patent document 1: Hindman J. C., "Proton Resonance Shift of Water in the Gas and Liquid States", The Journal Of Chemical Physics, 1966, Vol. 44, pp. 4582-4592

Non-patent document 2: Cady E. B. et al., "The Estimation of Local Brain Temperature by In Vivo 1H Magnetic Resonance Spectroscopy", Magnetic Resonance in Medicine, 1995, Vol. 33, pp. 862-867

DISCLOSURE OF THE INVENTION

Object to be Achieved by the Invention

In such a temperature information calculation method based on fitting utilizing a model function as mentioned above, the result of the fitting is influenced by the quality of spectra, such as half-hand width of the peak and signal to noise ratio, which results in variation of the calculated temperature. However, in this method, the operator cannot grasp accuracy of the calculated temperature. Since the accuracy (reliability) of the calculated temperature is information indispensable to the diagnosis, the temperature must be calculated from a plurality of times of measurement, and the accuracy of the calculated temperature must be confirmed on the basis of the standard deviation of the calculated temperatures etc. For this reason, the measurement of temperature of one test subject requires much time, and the subject also suffers from a heavy burden.

The present invention was accomplished in light of the above-mentioned circumstances, and an object thereof is to provide a technique for obtaining information of temperature in a living body and accuracy information thereof in a short time with low burden imposed on subject.

Means for Achieving the Object

According to the present invention, not only temperature information, but also accuracy thereof are calculated from spectra obtained by one time of MRS/MRSI measurement for each of two kinds of substances showing different resonant frequencies, and the accuracy is presented to an operator together with the temperature information.

Specifically, the present invention provides a magnetic resonance imaging apparatus having a static magnetic field generator configured to generate a static magnetic field in a space in which a subject is placed, a radio frequency magnetic field irradiator configured to irradiate a radio frequency magnetic field on the subject, a gradient magnetic field applicator configured to apply a gradient magnetic field to the subject, a detector configured to detect magnetic resonance signals generated from the subject, a scan controller configured to obtain magnetic resonance signals of two kinds of substances showing different resonant frequencies by controlling operations of the gradient magnetic field applicator, the radio frequency magnetic field irradiator, and the detector, an arithmetic unit configured to carry out operational processing of the magnetic resonance signals, and a display device configured to display information obtained by the operational processing, wherein the arithmetic unit is provided with a spectrum calculator configured to calculate spectra of magnetic resonance signals of the two kinds of substances showing different resonant frequencies, a temperature information calculator configured to calculate temperature information for inside of the subject on the basis of peaks of the calculated spectra, a temperature accuracy information calculator configured to calculate temperature accuracy information indicating accuracy of the temperature information on the basis of peaks of the calculated spectra, and a display information generator configured to generate display information to be displayed on the display device on the basis of the temperature information and the temperature accuracy information.

Effect of the Invention

According to the present invention, temperature information for inside of a living body and accuracy information thereof can be obtained in a short time with low burden imposed on a subject.

BRIEF DESCRIPTION OF THE DRAWINGS

FIG. 7 is a flowchart of temperature information calculation processing according to an embodiment of the present invention.

FIG. 13 is a flowchart of another example of high resolution temperature difference image generation processing according to an embodiment of the present invention.

MODES FOR CARRYING OUT THE INVENTION

Hereafter, an embodiment of the present invention will be explained. In the following explanation, elements having the same function are indicated with the same numerals in all the drawings for explaining the embodiment, and repetitive explanation thereof is omitted.

Figure 1A:
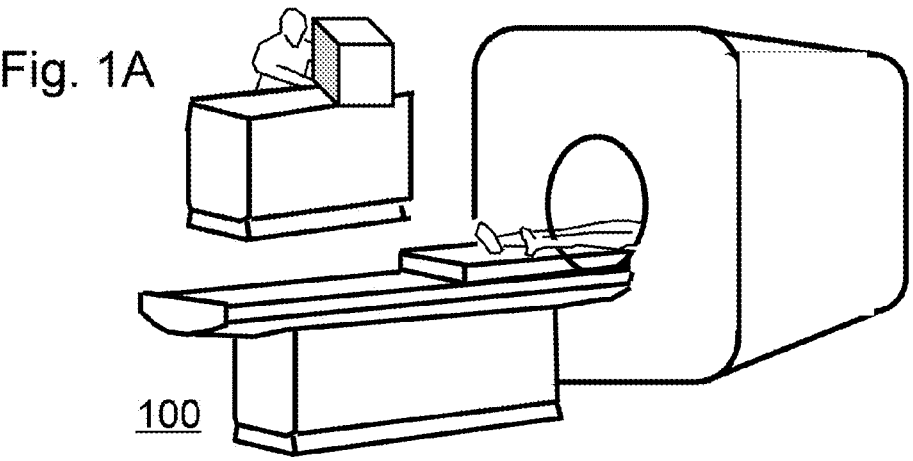
FIG. 1A is an external view of a magnetic resonance imaging apparatus according to an embodiment of the present invention.
Figure 1B:
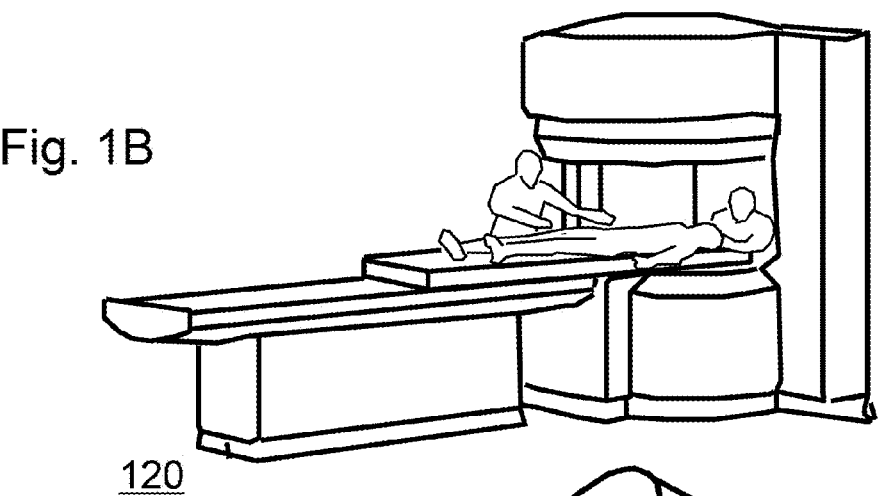
FIG. 1B is an external view of another magnetic resonance imaging apparatus according to an embodiment of the present invention.
Figure 1C:
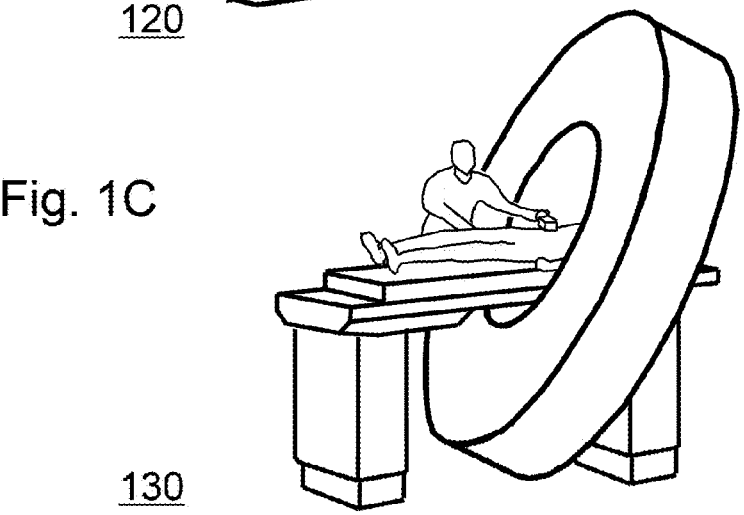
FIG. 1C is an external view of another magnetic resonance imaging apparatus according to an embodiment of the present invention.

First, magnetic resonance imaging apparatuses (MRI apparatuses) according to this embodiment will be explained. FIGS. 1A to 1C are external views of MRI apparatuses according to this embodiment. FIG. 1A shows an MRI apparatus 100 of the horizontal magnetic field type utilizing a tunnel-shaped magnet that generates a static magnetic field with a solenoid coil. FIG. 1B shows an MRI apparatus 120 of the vertical magnetic field type utilizing a hamburger type (open type) magnet provided with separated upper and lower magnets, which are used for increasing spaciousness. Further, FIG. 1C shows an MRI apparatus 130 utilizing a tunnel-shaped magnet similar to that of FIG. 1A, but depth of the magnet is shortened, and the magnet is leaned to increase spaciousness. For this embodiment, any of MRI apparatuses having these external views can be used. These are mere examples, and the MRI apparatus according to this embodiment is not limited to these apparatuses. For this embodiment, various kinds of known MRI apparatuses can be used regardless of form or type thereof. The following explanation will be made for the MRI apparatus 100 as a representative MRI apparatus, unless it is necessary to distinguish these types of apparatuses.

Figure 2:
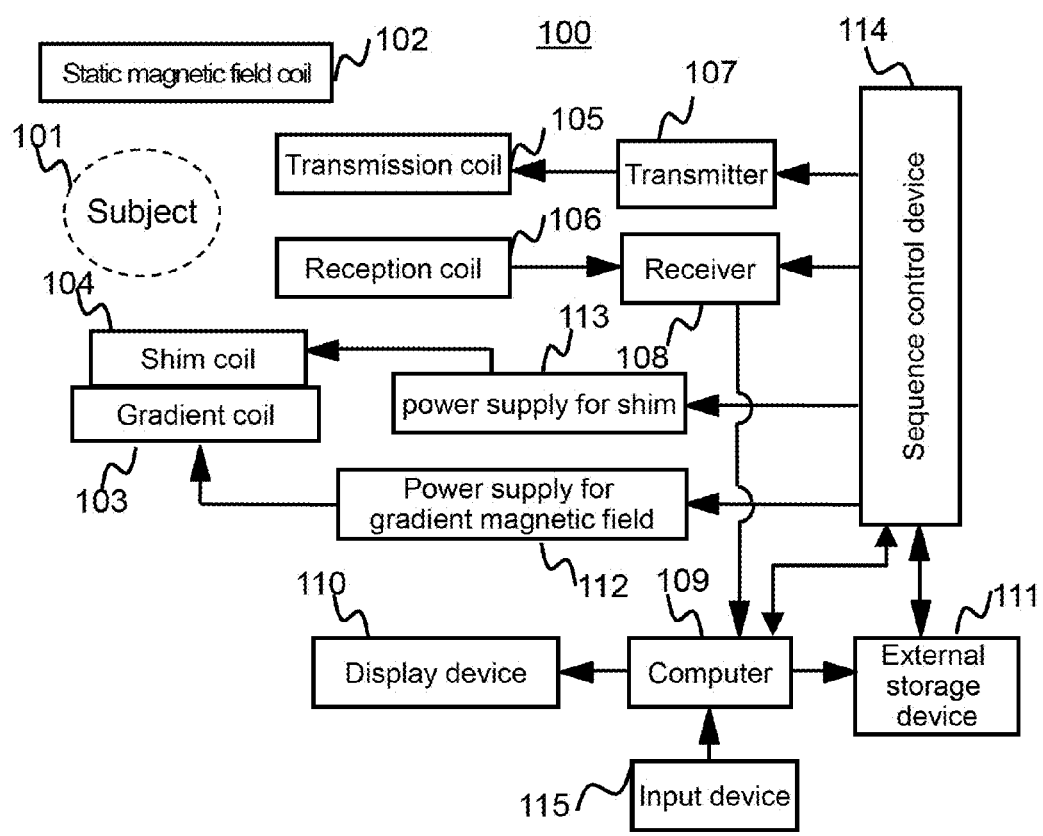
FIG. 2 is a functional and configurational diagram of a magnetic resonance imaging apparatus according to an embodiment of the present invention.

FIG. 2 is a functional and configurational diagram of the MRI apparatus 100 of this embodiment. As shown in this drawing, the MRI apparatus 100 of this embodiment is provided with the static magnetic field generator constituted with a static magnetic field coil 102 which generates a static magnetic field in a space in which a subject 101 is placed and so forth, a gradient coil 103 (gradient magnetic field applicator) configured to generate gradient magnetic fields in the x-, y-, and z-directions and apply them to the subject 101, a shim coil 104 configured to adjust static magnetic field distribution, a radio frequency magnetic field irradiation coil 105 (henceforth simply referred to as transmission coil, radio frequency magnetic field irradiator) configured to irradiate a radio frequency magnetic field on a measurement region of the subject 101, a magnetic resonance signal reception coil 106 (henceforth simply referred to as reception coil, detector) configured to detect magnetic resonance signals generated from the subject 101, a transmitter 107, a receiver 108, a computer 109, a power supply 112 for gradient magnetic field, a power supply 113 for shim, and a sequence control device 114.

There is employed the static magnetic field coil 102 chosen from those of various types according to the structure of the MRI apparatus such as those of the MRI apparatuses 100, 120, and 130 shown in FIGS. 1A, 1B, and 1C, respectively. The gradient coil 103 and the shim coil 104 are driven by the power supply 112 for gradient magnetic field, and the power supply 113 for shim, respectively. Although this embodiment is explained with reference to an example in which the transmission coil 105 and the reception coil 106 are separately provided, the apparatus may be constituted with one coil functionally serving as both the transmission coil 105 and the reception coil 106. The radio frequency magnetic field irradiated by the transmission coil 105 is generated by the transmitter 107. The magnetic resonance signals detected by the reception coil 106 are sent to the computer 109 via the receiver 108.

According to directions from the computer 109, the sequence control device 114 controls operations of the power supply 112 for gradient magnetic field, which is a power supply configured to drive the gradient coil 103, the power supply 113 for shim, which is a power supply configured to drive the shim coil 104, the transmitter 107, and the receiver 108, and thereby controls timings of applications of the gradient magnetic fields and radio frequency magnetic fields, and reception of magnetic resonance signals. The time chart for the control is called pulse sequence, which is set beforehand according to the measurement, and stored in a storage device or the like provided in the computer 109 explained later.

The computer 109 performs various operational processings for the received magnetic resonance signals to generate image information, spectrum information, temperature information, and temperature accuracy information, and gives directions to the sequence control device 114 to control the operations of the whole MRI apparatus 100. The computer 109 is an information processor having CPU, memory, storage device, and so forth, and the display device 110 such as a display, an external storage device 111, an input device 115, and so forth are connected to the computer 109.

The display device 110 is an interface for displaying results obtained by the operational processings, and so forth to an operator. The input device 115 is an interface for an operator to input conditions, parameters and so forth required for the operational processings performed in this embodiment. Together with the storage device, the external storage device 111 stores data used for various kinds of the operational processings performed by the computer 109, data obtained by the operational processings, inputted conditions, parameters, and so forth.

Figure 3:
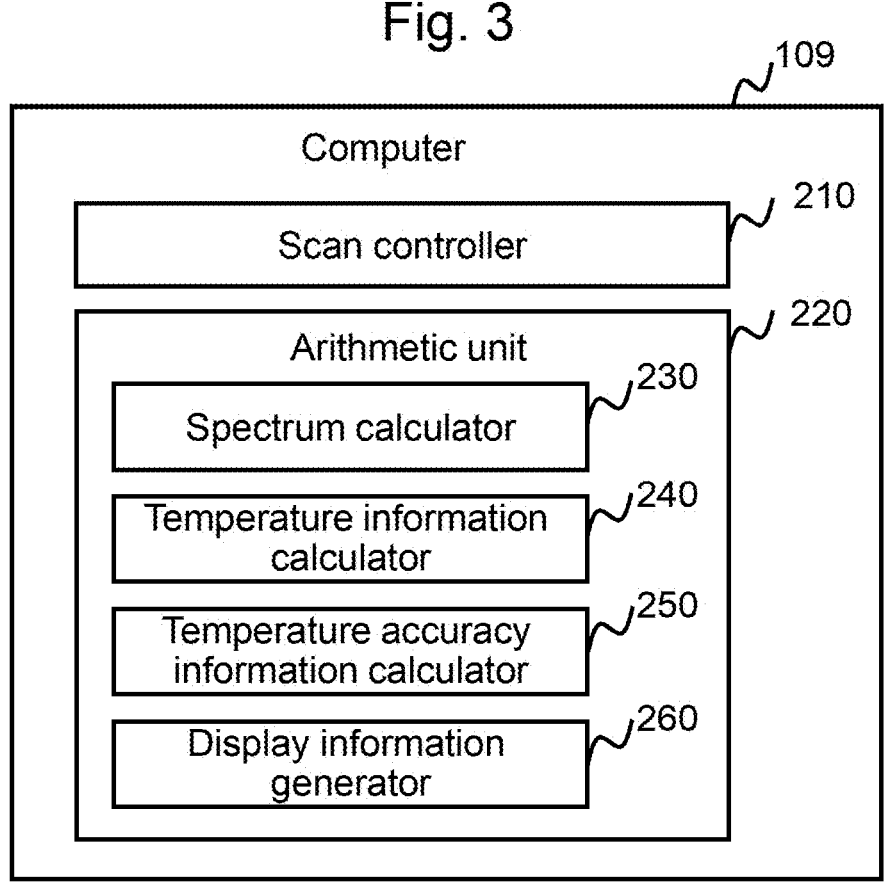
FIG. 3 is a functional block diagram of a computer provided in a magnetic resonance imaging apparatus according to an embodiment of the present invention.

As described above, the MRI apparatus 100 of this embodiment calculates temperature information and index indicating accuracy (reliability) of the temperature information through one time of measurement. The function of the computer 109 of this embodiment for performing the above operation will be explained. FIG. 3 is a functional block diagram of the computer 109 of this embodiment.

As shown in this drawing, the computer 109 of this embodiment is provided with a scan controller 210 and an arithmetic unit 220. The scan controller 210 performs measurement by operating the sequence control device 114 and controlling every component according to a pulse sequence, and thereby obtains magnetic resonance signals. The arithmetic unit 220 performs various operational processings for the magnetic resonance signals obtained by the measurement to generate image information, spectrum information, temperature information, temperature accuracy information, and so forth.

The arithmetic unit 220 converts the magnetic resonance signals obtained by the measurement into a spectrum, calculates temperature information and temperature accuracy information, and generates display information to be displayed on the display device 110. In order to perform the above operation, the arithmetic unit 220 of this embodiment is provided with a spectrum calculator 230 configured to convert the magnetic resonance signals obtained by the measurement into a spectrum, a temperature information calculator 240 configured to calculate temperature information in the inside of the subject 101 from the spectrum, a temperature accuracy information calculator 250 configured to calculate accuracy of the calculated temperature information, and a display information generator 260. According to this embodiment, the temperature accuracy information calculator 250 calculates temperature accuracy information also by using the spectrum with which the temperature information calculator 240 calculates the temperature information.

The various kinds of functions of the computer 109 are realized by CPU by loading programs stored in the storage device in a memory and executing them. At least one of the various kinds of functions of the computer 109 may be realized by an information processor independent from the MRI apparatus 100, which can transmit and receive data to and from the MRI apparatus 100.

Figure 4:
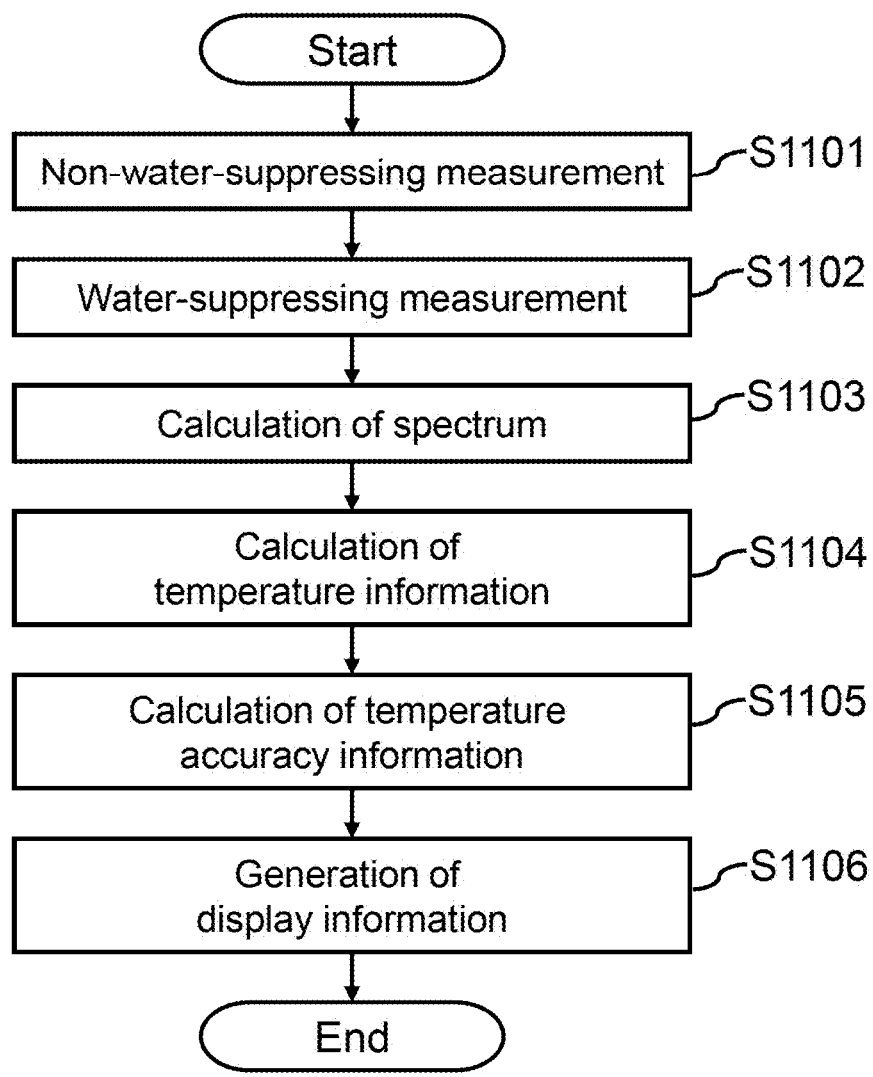
FIG. 4 is a flowchart for explaining flow of the whole temperature information and temperature accuracy information calculation measurement according to an embodiment of the present invention.

Hereafter, the flow of the whole temperature information and temperature accuracy information calculation measurement of this embodiment performed by the computer 109 of this embodiment with the functions thereof will be explained briefly. FIG. 4 shows the process flow of the whole temperature information and temperature accuracy information calculation measurement of this embodiment. In this embodiment, in order to calculate temperature information and temperature accuracy information, spectrum information on two kinds of substances showing difference of resonant frequencies is used. This characteristic of this embodiment will be explained below for a case of using water and a metabolite (NAA) as the two kinds of substances showing difference of resonant frequencies as an example.

First, the scan controller 210 performs non-water-suppressing measurement (Step S1101) to obtain magnetic resonance signals of water. Then, it performs water-suppressing measurement (Step S1102) to obtain magnetic resonance signals of the metabolite. Both the non-water-suppressing measurement and the water-suppressing measurement are realized by controlling the sequence control device 114 according to a predetermined pulse sequence. An example of such a predetermined pulse sequence will be mentioned later. Although the magnetic resonance signals of water and NAA are obtained by separate measurements in this explanation of this embodiment, the magnetic resonance signals of water and NAA may be obtained simultaneously by performing the measurement with not completely suppressing the water signals, but with leaving a certain level of water signal amount to remain, or the like.

Then, the spectrum calculator 230 carries out the Fourier transform of the obtained magnetic resonance signals of water and NAA to calculate spectra of water and NAA (Step S1103). Then, the temperature information calculator 240 calculates temperature in the subject (temperature information) from the spectra of water and NAA (Step S1104). Further, the temperature accuracy information calculator 250 calculates an index indicating temperature accuracy (temperature accuracy information) from the spectra of water and NAA (Step S1105). Then, the display information generator 260 generates display information from the calculated temperature information and temperature accuracy information, and displays them on the display device 110 (Step S1106).

Examples of the pulse sequence for the non-water-suppressing measurement and the water-suppressing measurement executed by the scan controller 210 in Steps S1101 and S1102 mentioned above, respectively, will be explained below. The following explanation will be made for a pulse sequence for the region selecting magnetic resonance spectroscopic imaging, which images metabolite (henceforth referred to as MRSI sequence) as an example.

Figure 5:
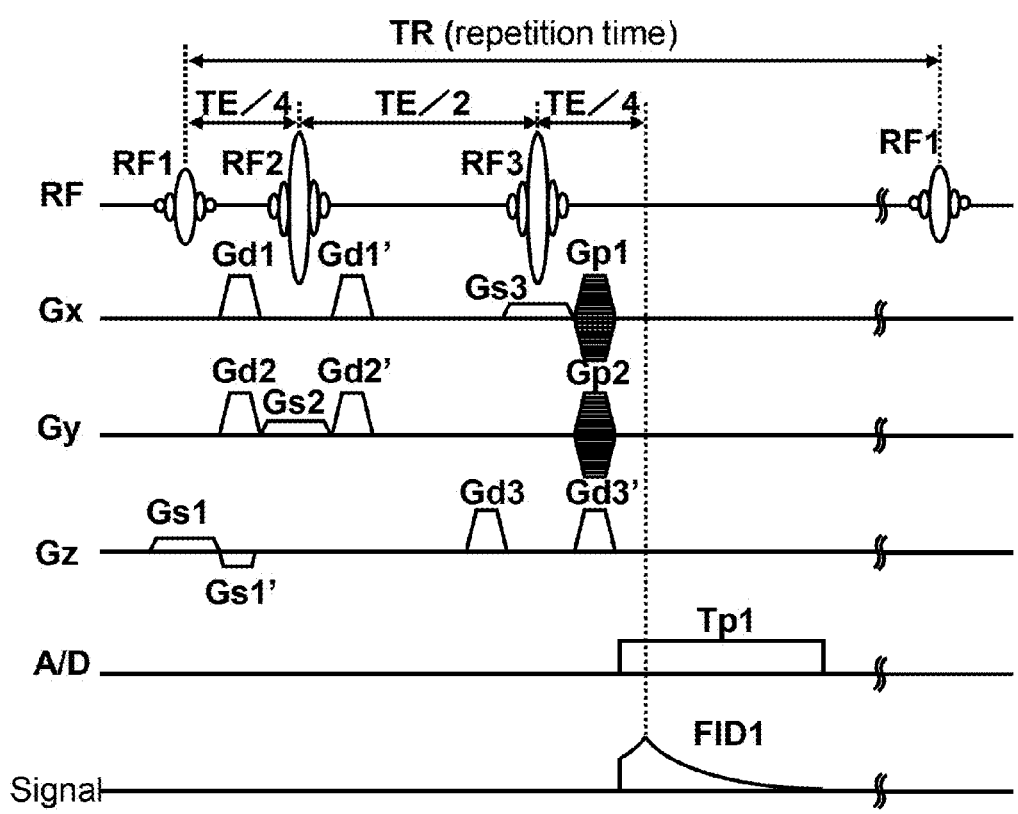
FIG. 5 is an explanatory drawing for explaining an example of MRSI sequence used in an embodiment of the present invention.

FIG. 5 shows an example of the MRSI sequence 300. In FIG. 5, RF represents application timings of radio frequency magnetic field pulses. Gx, Gy, and Gz represent application timings of gradient magnetic field pulses for the x-, y-, and z-directions, respectively. A/D represents signal measurement period. The MRSI sequence 300 shown in FIG. 5 is the same as known MRSI sequences, and it is for selectively exciting a predetermined region of interest (voxel) by using one excitation pulse RF1 and two inversion pulses RF2 and RF3, and obtaining an FID (free induction decay) signal FID1 from the region of interest (voxel).

Figure 6A:
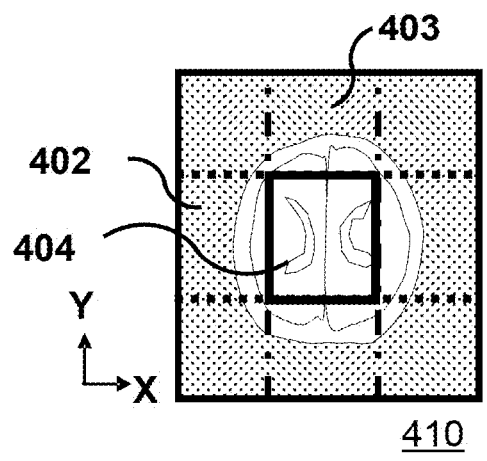
FIG. 6A is an explanatory drawing for explaining a region to be excited with an MRSI sequence used in an embodiment of the present invention.
Figure 6B:
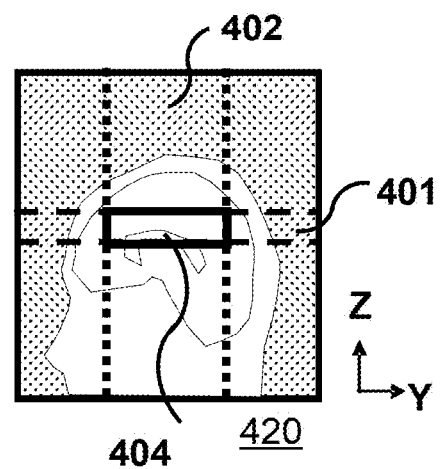
FIG. 6B is an explanatory drawing for explaining a region to be excited with an MRSI sequence used in an embodiment of the present invention.
Figure 6C:
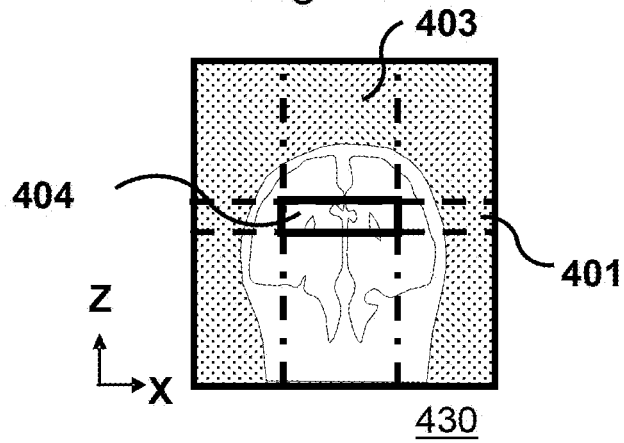
FIG. 6C is an explanatory drawing for explaining a region to be excited with an MRSI sequence used in an embodiment of the present invention.

The region excited with this MRSI sequence 300 is shown in FIG. 6. FIG. 6 shows scout images for positioning obtained by measurement performed in advance of the main measurement, and FIGS. 6A, 6B, and 6C show a transverse image 410, a sagittal image 420, and a coronal image 430, respectively. Hereafter, the relation between the operations of the components and the region to be excited will be explained with reference to FIGS. 5, 6A, 6B, and 6C.

A radio frequency magnetic field RF1, and gradient magnetic field pulses Gs1 and Gs1' for the z-direction are first applied to excite a section 401 of the z-direction. After the time of TE/4 (TE is echo time), a radio frequency magnetic field RF2 and gradient magnetic field pulse Gs2 for the y-direction are applied. As a result, only the phase of the nuclear magnetization in the crossing region of the section 401 of the z-direction and the section 402 of the y-direction is rephased (returned). Then, after the time of TE/2 from the application of the radio frequency magnetic field RF2, a radio frequency magnetic field RF3 and a gradient magnetic field pulse Gs3 of the x-direction are applied. Only the phase of the nuclear magnetization in the region of interest (voxel) 404 where the section 401 of the z-direction, the section 402 of the y-direction, and the section 403 of the x-direction are crossing is thereby rephased, and a free induction decay signal FID1 is generated therefrom. This free induction decay signal FID1 is measured. The gradient magnetic field pulses Gd1 to Gd3 and Gd1' to Gd3' for the respective directions are gradient magnetic fields for rephasing the phase of the nuclear magnetization excited by the radio frequency magnetic field RF1, and dephasing the phase of the nuclear magnetization excited by RF2 and RF3. Further, after the application of the radio frequency magnetic field RF3, the phase encoding gradient magnetic fields Gp1 and Gp2 are applied. By the above operation, magnetic resonance signals of the region of interest (voxel) 404 are obtained.

As described above, the spectrum calculator 230 of this embodiment performs the Fourier transform of the magnetic resonance signals of water and NAA of the region of interest (voxel) 404, which have been measured with the MRSI sequence 300 in Step S1103 mentioned above, for the time direction to calculate spectra of water and NAA of the region of interest (voxel) 404.

Hereafter, the calculation of the temperature information performed by the temperature information calculator 240 in Step S1104 mentioned above will be explained. The temperature information calculator 240 of this embodiment calculates resonant frequencies of water and NAA, and converts the difference of them (difference of resonant frequency) into temperature to obtain the temperature information of each region of interest (voxel) 404. The resonant frequencies of water and NAA are obtained by fitting the spectral peaks of water and NAA with a predetermined function.

The flow of the temperature information calculation processing performed by the temperature information calculator 240 of this embodiment will be explained. FIG. 7 shows the process flow of the temperature information calculation processing of this embodiment.

First, the temperature information calculator 240 calculates the resonant frequencies of water and NAA (Step S4101). According to this embodiment, the obtained spectral peaks of water and NAA are fitted by using the Lorenz type function represented by the equation (1), or the like to obtain the resonant frequency of water $v_W$ and the resonant frequency of NAA $v_{NAA}$, respectively.

Then, the temperature information calculator 240 calculates the difference of the resonant frequency of water $v_W$ and the resonant frequency of NAA $v_{NAA}$ to calculate resonant frequency difference $\Delta v$ (Step S4102).

Then, the temperature information calculator 240 calculates the temperature information by converting the frequency difference into temperature using the temperature conversion equation for converting frequency difference into temperature (Step S4103). The temperature conversion equation is created beforehand and stored in the storage device, or the like. An example of the temperature conversion equation used in this embodiment is shown as the equation (2).

$$T = p \times \Delta v + q \qquad (2)$$

In the equation, T represents temperature, p represents a coefficient having the dimension of temperature/frequency, and q is a constant term. As the values of p and q in the equation (2), known values described in literature or experimentally calculated values are used.

Next, the calculation of the temperature accuracy information performed by the temperature accuracy information calculator 250 in Step S1105 mentioned above will be explained. The temperature accuracy information calculator 250 of this embodiment determines model functions representing spectral peaks of water and NAA, then by adding random noises to the model functions a plurality of times, a plurality of kinds of virtual temperature information is obtained, and subjected to a statistical treatment to obtain temperature accuracy information of the temperature information for each region of interest (voxel) 404. The model functions are changed by adding a plurality of kinds of different noises equivalent to the noises obtained from the spectra obtained by the measurement. According to this embodiment, for example, a standard deviation of the noises obtained from the spectrum is calculated, and a group of noises is generated in the same manner as that of random number generation, and added to the model functions.

Figure 8:
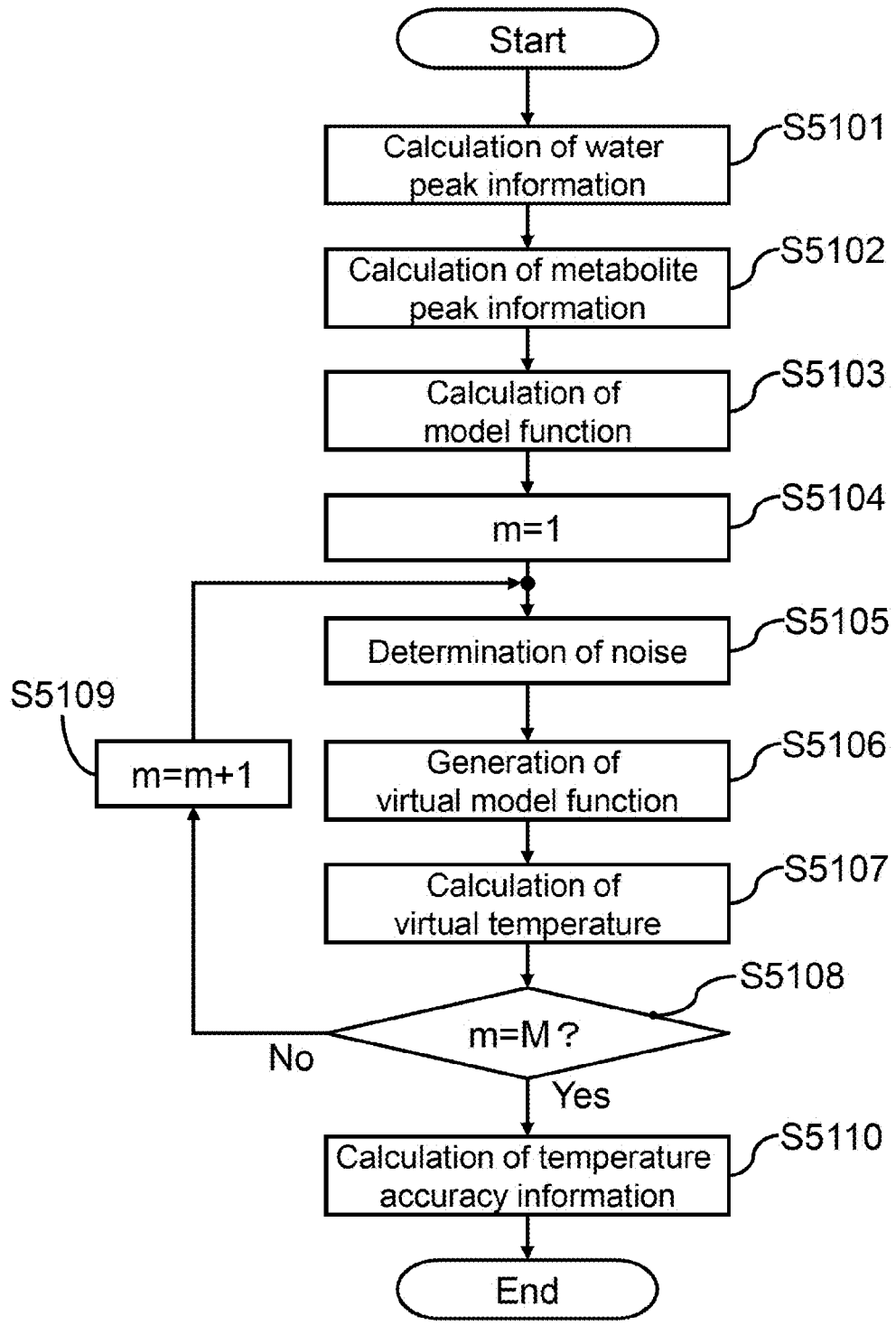
FIG. 8 is a flowchart of temperature accuracy information calculation processing according to an embodiment of the present invention.

The flow of the temperature accuracy information calculation processing performed by the temperature accuracy information calculator 250 of this embodiment is explained. FIG. 8 shows the process flow of the temperature accuracy information calculation processing of this embodiment.

First, the temperature accuracy information calculator 250 calculates water peak information and standard deviation of noises of water (Step S5101).

The water peak information used in this embodiment includes parameters of the function used for the fitting. For example, when the Lorenz type function shown as the equation (1) is used for the fitting, the information includes the resonant frequency $v_W$ of water, half-hand width $a_W$ of spectral peak, height $I_W$ of spectral peak, phase $\phi_W$, and constant term $c_W$. In this explanation, the measured water peak is fitted by using the Lorenz type function shown as the equation (1) to determine the parameters of the function used. Specifically, the resonant frequency $v_W$ of water, half-hand width $a_W$ of spectral peak, height $I_W$ of spectral peak, phase $\phi_W$, and constant term $c_W$ are obtained.

Further, standard deviation $\sigma_W$ of the noises of water is calculated by using a plurality of signal values $N_W$ within a noise region (region of no signal of water or metabolite) of the obtained spectrum of water. Together with the standard deviation of the noises, signal to noise ratio ($SNR_W$) may be further calculated. If the standard deviation of the noises of the spectrum of water is represented as $\sigma_W$, the signal to noise ratio $SNR_W$ of water is calculated as $I_W/\sigma_W$.

Then, the temperature accuracy information calculator 250 calculates peak information of the metabolite (NAA) and standard deviation of noises of NAA (step S5102).

The NAA peak information calculated in this embodiment is information similar to the aforementioned water peak information. Therefore, in the same manner as the aforementioned method for calculating the information of water peak, the measured NAA peak is fitted by using the Lorenz type function shown as the equation (1) to determine the parameters of the function used. Specifically, the resonant frequency $v_{NAA}$ of NAA peak, half-hand width $a_{NAA}$ of spectral peak, height $I_{NAA}$ of spectral peak, phase $\phi_{NAA}$, and constant term $c_{NAA}$ are calculated.

Further, standard deviation $\sigma_{NAA}$ of the noises of NAA is calculated by using a plurality of signal values $N_{NAA}$ within a noise region of the obtained spectrum of NAA. Also for NAA, signal to noise ratio ($SNR_{NAA}$) may be further calculated. If the standard deviation of the noises of the spectrum of NAA is represented as $\sigma_{NAA}$, the signal to noise ratio $SNR_{NAA}$ of NAA is calculated as $I_{NAA}/\sigma_{NAA}$.

Then, the temperature accuracy information calculator 250 calculates a model function of the frequency v by using the water peak information and the NAA peak information (Step S5103). According to this embodiment, the Lorenz type function shown as the equation (1) used for the fitting as the model function. A model function $L_W(v)$ of water is calculated by using the water peak information, and a model function $L_{NAA}(v)$ of NAA is calculated by using the NAA peak information.

Then, the temperature accuracy information calculator 250 calculates virtual temperatures from a plurality of virtual spectra created by adding virtual noises to the model functions, respectively. According to this embodiment, M (M is a natural number) of virtual temperatures are calculated. Therefore, the temperature accuracy information calculator 250 first sets number of a counter m (m is an integer of 1 to M) to be 1 (Step S5104).

Then, the temperature accuracy information calculator 250 determines virtual noises $N_W(v)$ and $N_{NAA}(v)$ of the same standard deviations as the noise standard deviations $\sigma_W$ and $\sigma_{NAA}$ for water and NAA at random by using, for example, random numbers (Step S5105). The determined m-th virtual noises $N_W(v, m)$ and $N_{NAA}(v, m)$ satisfy the following equations (3) and (4), respectively.

$$\mathrm{var}(N_W(v,m)) = \sigma_W^2 \qquad (3)$$

$$\mathrm{var}(N_{NAA}(v,m)) = \sigma_{NAA}^2 \qquad (4)$$

var( ) is an operator for calculating a standard deviation of the variable mentioned in the parentheses.

Then, as shown in the following equations (5) and (6), the temperature accuracy information calculator 250 adds the determined noises $N_W(v, m)$ and $N_{NAA}(v, m)$ to the model functions $L_W(v)$ and $L_{NAA}(v)$, respectively, to generate the model functions (virtual model functions) $L_W(v, m)$ and $L_{NAA}(v, m)$ including the added m-th virtual noise (Step S5106).

$$L_W(v,m)m = L_W(v) + N_W(v,m) \qquad (5)$$

$$L_{NAA}(v,m)m = L_{NAA}(v) + N_{NAA}(v,m) \qquad (6)$$

According to the above-mentioned procedure, the temperature accuracy information calculator 250 obtains the virtual model functions $L_W(v, m)$ and $L_{NAA}(v, m)$, which give the same standard deviations $\sigma_W$ and $\sigma_{NAA}$ of noises that spectra of water and spectra of NAA calculated by the spectrum calculator 230 give.

If the signal to noise ratio ($SNR_W$) of water peak and the signal to noise ratio ($SNR_{NAA}$) of NAA peak are calculated, the virtual model functions may be determined so that the signal to noise ratios becomes equal to them.

Then, the temperature accuracy information calculator 250 calculates virtual temperatures from the virtual model functions $L_W(v, m)$ and $L_{NAA}(v, m)$ (Step S5107). The processing for the calculation of the virtual temperatures is similar to the processing of the temperature information calculation performed by the aforementioned temperature information calculator 240. Specifically, the virtual model functions $L_W(v, m)$ and $L_{NAA}(v, m)$ are fitted with the Lorenz type function of the equation (1) to calculate the resonant frequencies $v_W(m)$ and $v_{NAA}(m)$, respectively. Then, the resonant frequency difference $\Delta v(m)$ is calculated, and the m-th virtual temperature in the subject 101 is calculated by using a predetermined conversion equation (for example, the equation (2)).

Further, the temperature accuracy information calculator 250 repeats Steps S5104 to S5106 mentioned above M times to calculate M of the virtual temperatures (Steps S5108 and S5109). In this repetition, in Step S5105, the virtual noises $N_W(v, m)$ and $N_{NAA}(v, m)$ showing the same standard deviations as the noise standard deviations $\sigma_W$ and $\sigma_{NAA}$ are determined in the same manner as that of generation of random numbers.

Finally, the temperature accuracy information calculator 250 calculates standard deviation $\sigma_T$ for M of the virtual temperatures as an index of temperature accuracy (temperature accuracy information) (Step S5110).

According to the aforementioned procedure, the temperature accuracy information calculator 250 of this embodiment calculates the temperature accuracy information (standard deviations in this case) that serves as an index of the temperature accuracy of the temperatures calculated from the spectra of water and NAA obtained by the measurements in Steps S1101 and S1102 mentioned above.

In the above explanation of this embodiment, the standard deviation $\sigma_T$ for M of the virtual temperatures is calculated as the temperature accuracy information. However, the temperature accuracy information is not limited to it. M of the obtained virtual temperatures can be subjected to a statistical treatment to calculate various kinds of values that serve as index of temperature accuracy as the temperature accuracy information. The temperature accuracy information may be, for example, dispersion, standard error, or the like.

Figure 9:
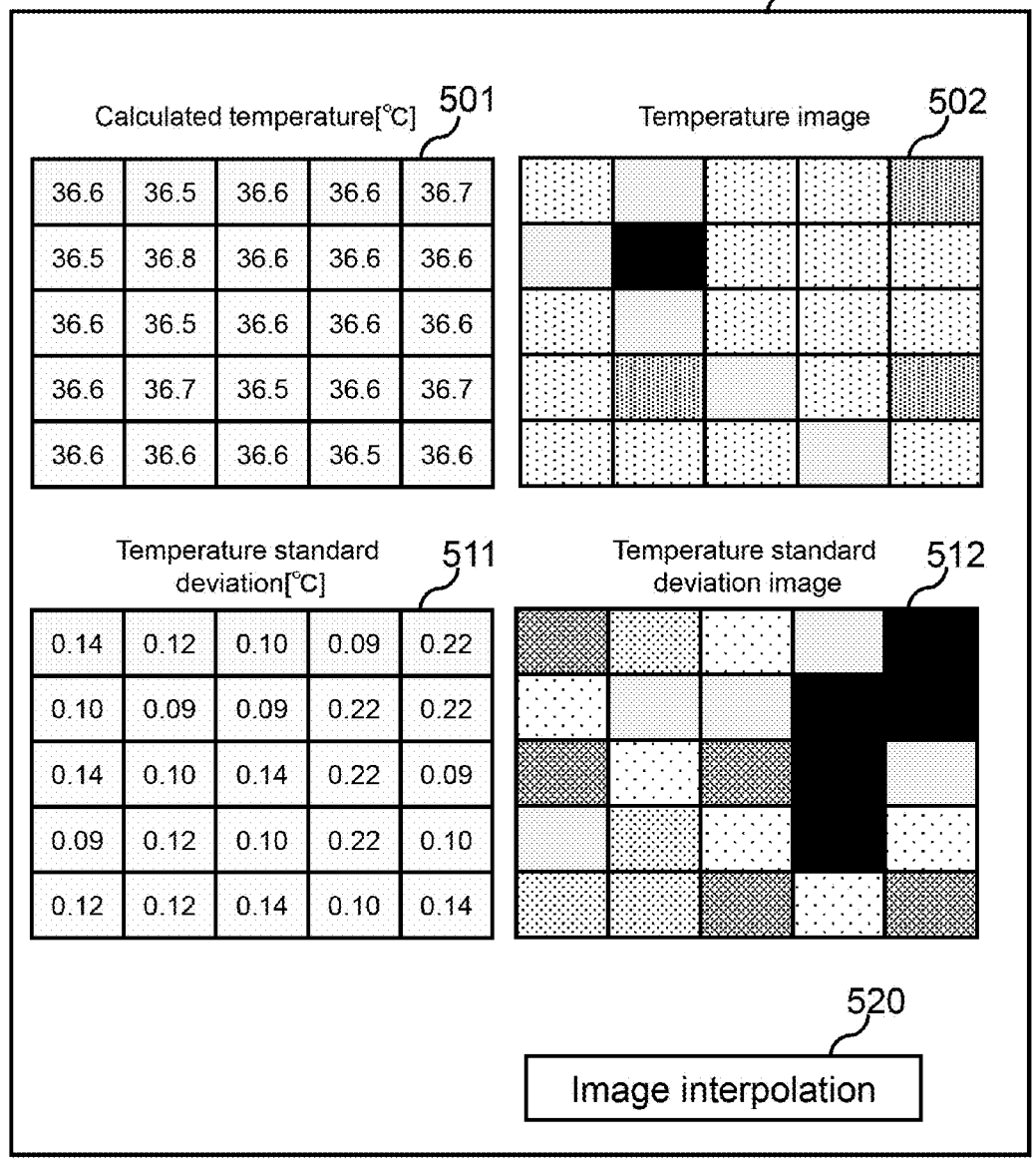
FIG. 9 is an explanatory drawing for explaining an example of display of display information generated by the display information generator according to an embodiment of the present invention.

Hereafter, the display information of this embodiment calculated by the display information generator 260 in Step S1106 mentioned above will be explained. FIG. 9 includes explanatory diagrams for explaining the display information displayed on a display screen 116 of the display device 110 of this embodiment.

The display information generated by the display information generator 260 of this embodiment includes, for example, a temperature table 501 that indicates the temperature information of the regions of interest (voxels) 404 calculated by the temperature information calculator 240 in a matrix measured with the MRSI sequence 300 in a corresponding manner, a temperature image 502 of which pixel values are the values of the temperature table 501, a temperature accuracy table 511 that indicates the temperature accuracy information of the regions of interest (voxels) 404 calculated by the temperature accuracy information calculator 250 in a matrix measured with the MRSI sequence 300 in a corresponding manner, and a temperature accuracy image 512 of which pixel values are the values of the temperature accuracy table 511.

Further, instead of the temperature image 502, a temperature difference image may be calculated as the display information. The temperature difference image is obtained by subtracting temperature of a reference voxel, which may be an arbitrary voxel, from the temperatures of the voxels other than the reference voxel.

The display information to be displayed on the display device 110 is not limited to such information as mentioned above. The display information may include various operation results, such as water peak information, and NAA peak information, which are obtained in the middle of the calculation of the temperature information and the temperature accuracy information. Further, the temperature information, temperature accuracy information, water peak information, and NAA peak information may be displayed for every voxel of the matrix measured with the MRSI sequence 300. Further, the temperature image and the temperature difference image may be superimposingly displayed on various images, such as MR image, CT image, PET image, and SPECT image.

As explained above, the MRI apparatus 100 of this embodiment is a magnetic resonance imaging apparatus having a static magnetic field generation means (static magnetic field generator) for generating a static magnetic field in a space in which a subject is placed (static magnetic field coil 102), a radio frequency magnetic field irradiation means (radio frequency magnetic field irradiator) for irradiating a radio frequency magnetic field on the subject (transmission coil 105), a gradient magnetic field application means (gradient magnetic field applicator) for applying a gradient magnetic field to the subject (gradient coil 103), a detecting means (detector) for detecting magnetic resonance signals generated from the subject (reception coil 106), a scan control means (scan controller) 210 for obtaining magnetic resonance signals of two kinds of substances showing different resonant frequencies by controlling operations of the gradient magnetic field applicator, the radio frequency magnetic field irradiator, and the detector, an operation means (arithmetic unit) 220 for carrying out operational processing of the magnetic resonance signals, and a display means (display device) 110 for displaying information obtained by the operation processing, wherein the arithmetic unit 220 is provided with a spectrum calculation means (spectrum calculator) 230 for calculating spectra of magnetic resonance signals of two kinds of the substances showing difference of resonant frequencies, a temperature information calculation means (temperature information calculator) 240 for calculating temperature information for the inside of the subject on the basis of the calculated spectral peaks, a temperature accuracy information calculation means (temperature accuracy information calculator) 250 for calculating temperature accuracy information indicating accuracy of the temperature information on the basis of the calculated spectral peaks, and a display information generating means (display information generator) 260 for generating display information to be displayed on the display device 110 on the basis of the temperature information and the temperature accuracy information.

The temperature information calculator 240 is provided with a resonant frequency calculation means (resonant frequency calculator) for determining functions representing the calculated spectral peaks, and for calculating resonant frequencies of the two kinds of substances on the basis of the functions, and a conversion means (converter) for converting difference of two of the resonant frequencies determined above into temperature information. Further, the temperature accuracy information calculator 240 is provided with a model function calculation means (model function calculator) for calculating model functions representing the respective calculated spectral peaks, a virtual model function generating means (virtual model function generator) for generating a plurality of virtual model functions for each of the two kind of substances by adding a plurality of virtual noises to each of the determined model functions, and a virtual temperature calculation means (virtual temperature calculator) for calculating virtual temperature from each of the virtual model functions, and the temperature information calculator 240 subjects a plurality of the virtual temperatures to a statistical treatment to obtain the temperature accuracy information.

As described above, according to this embodiment, by performing one time of MRS/MRSI measurement for each of a plurality kinds of substances showing difference of resonant frequencies, temperatures in a subject and accuracy information on the temperatures can be calculated, and presented to an operator. That is, temperature information concerning inside of a living body and accuracy information thereof can be obtained by one time of measurement for each of the plurality kinds of substances. Therefore, temperature of a subject and accuracy information thereof can be obtained in a short time by a method that imposes low burden on the subject.

Figure 10:
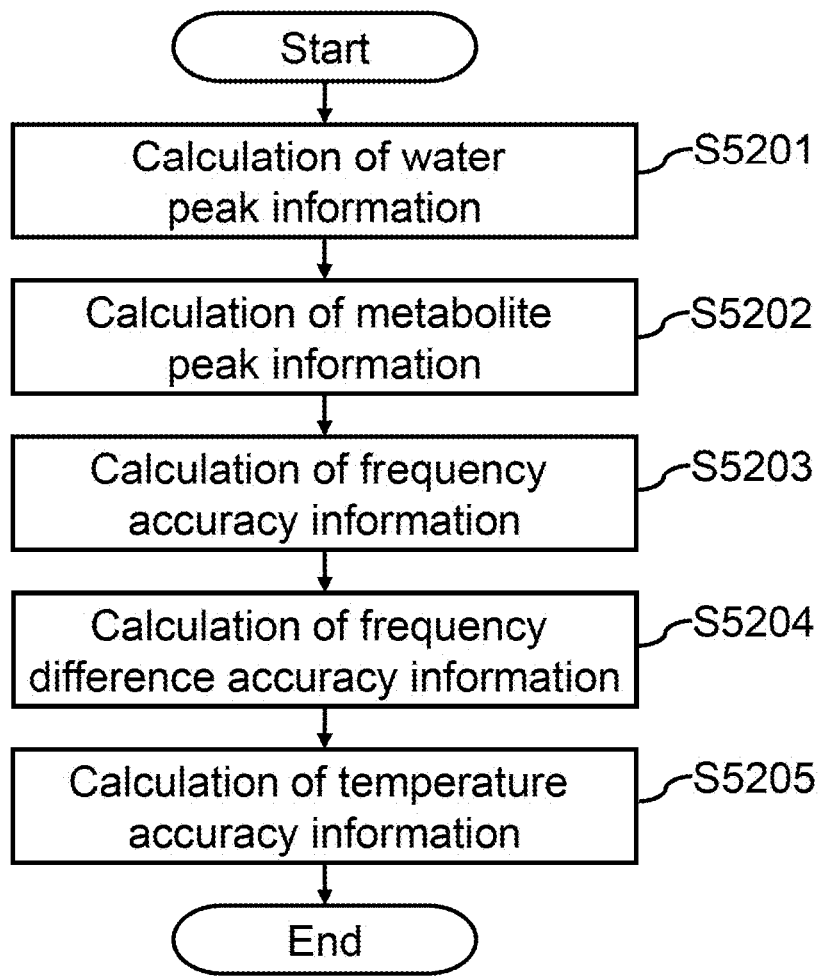
FIG. 10 is a flowchart of another example of temperature accuracy information calculation processing according to an embodiment of the present invention.

In the above explanation of this embodiment, the temperature accuracy information calculator 250 obtains a plurality of virtual temperatures, and calculates the temperature accuracy information. However, the method for calculating the temperature accuracy information is not limited to such a method. The temperature accuracy information may be obtained by numerical analysis method by using, for example, the error spreading method based on a model function. The temperature calculation method using the error spreading method is explained below. FIG. 10 shows a process flow of a temperature accuracy information calculation processing using the error spreading method according to this embodiment.

First, the temperature accuracy information calculator 250 calculates water peak information (Step S5201). This calculation is the same as that of Step S5101 mentioned above. Further, it also calculates metabolite (NAA) peak information (Step S5202). This is also the same as that of Step S5102 mentioned above. That is, the spectral peaks are fitted with model functions defined beforehand to determine coefficients of the model functions, and information of the peaks is thereby obtained.

Then, frequency accuracy information is calculated as an index of the accuracy of the peak frequency by using the error spreading method (Step S5203). In this explanation, standard deviation of peak frequencies is calculated as the frequency accuracy information. In the error spreading method used in this modified example, there are estimated amounts of errors of the parameters of the fitting functions (henceforth referred to as fitting parameters) to be generated when, for example, fitting of the measured spectral data is performed with the Lorenz type function shown as the equation (1), and the aforementioned standard deviation is calculated.

Hereafter, there will be explained a method for calculating the aforementioned standard deviation in which the fitting function is not limited to the Lorenz type function, but is generalized. For the following calculation, it is assumed that noise components $N(f_k)$ included in the measured spectral data of the points $f_k$ have the same distribution, the average thereof is 0, and the dispersion $\sigma^2$ is sufficiently small.

The fitting parameters of the function used as the fitting function are represented by a vector $B=\{b_i\}$. The deviation included in the measurement data of signal intensity $L(f_k)$ is represented by $\Delta L$. The relation between $\Delta L$ and the deviation $\Delta B$ included in the vector $B=\{b_i\}$ of the fitting parameters is given by the following approximate equation (7).

[Equation 7]

$$\Delta B = -\left\{\sum_{k=F1}^{F2} \frac{\partial L(B, f_k)}{\partial b_i} \frac{\partial L(B, f_k)}{\partial b_j}\right\}_{i,j}^{-1} \left(\sum_{k=F1}^{F2} \frac{\partial L(B, f_k)}{\partial b_i} \Delta L(f_k)\right) \quad (7)$$

In the equation, F1 and F2 represent end points of frequency region used for the fitting, $f_k$ represents frequency point, and L(B, f) represents a model function used for the fitting in which elements $b_i$ of B substitute for the corresponding parameters. For example, when the Lorenz type function is used for water peaks, the elements $b_i$ consist of the water peak information calculated in Step S5201, i.e., $b_1=\nu_W$, $b_2=I_W$, $b_3=a_W$, $b_4=\phi_W$, and $b_5=c_W$, and L(B, f) is represented by the equation (1) in which the elements of $b_i$ substitutes for the corresponding parameters.

From the assumption, $\Delta L(f_k)$ in the equation (7) can be regarded as the noise component $N(f_k)$, and therefore distribution of $\Delta B$ is given by the following equation (8).

[Equation 8]

$$\Delta B = -\left\{\sum_{k=F1}^{F2} \frac{\partial L(B, f_k)}{\partial b_i} \frac{\partial L(B, f_k)}{\partial b_j}\right\}_{i,j}^{-1} \left(\sum_{k=F1}^{F2} \frac{\partial L(B, f_k)}{\partial b_i} N(f_k)\right) \quad (8)$$

$$= \left(\sum_{k=F1}^{F2} D(B, F, k)_i N(f_k)\right)_i$$

In the equation, F represents a set of points f of the spectral data $\{f_k\}k=F1, \ldots F2$, and $D(B, F, k)_i$ represents coefficients of the noise components $N(f_k)$ defined in the equation (8). If the elements of $\Delta B$ are represented as $\Delta b_i$ on the basis of the assumption, the dispersion $\text{var}(\Delta b_i)$ is given by the following equation (9).

[Equation 9]

$$\text{var}(\Delta b_i) = \sum_{k=F1}^{F2} D(B, F, k)_i^2 \sigma^2 \quad (9)$$

Therefore, the standard deviation $\sigma_{W1}$ of the resonant frequencies of the water peaks $\nu_W$ (water peak frequencies) according to this embodiment can be calculated by obtaining the square root of $\text{var}(\Delta b_1)$ under the condition of i=1.

Similarly, standard deviation $\sigma_{NAA1}$ of the resonant frequencies $\nu_{NAA}$ of the NAA peaks (NAA peak frequencies) is calculated by substituting $b_1=\nu_{NAA}$, $b_2=I_{NAA}$, $b_3=a_{NAA}$, $b_4=\phi_{NAA}$, and $b_5=c_{NAA}$ for the corresponding parameters of $D(B, F, k)_i$, and obtaining the square root of $\text{var}(\Delta b_1)$ using the equation (8).

By the method described above, the standard deviation $\sigma_{W1}$ of the water peak frequencies $\nu_W$, and the standard deviation $\sigma_{NAA1}$ of the NAA peak frequencies $\nu_{NAA}$ can be calculated.

Then, from the standard deviation $\sigma_{W1}$ of the water peak frequencies $\nu_W$ and the standard deviation $\sigma_{NAA1}$ of the NAA peak frequencies $\nu_{NAA}$, frequency difference accuracy information (standard deviation) is calculated as an index of the accuracy of the peak frequency difference as spreading error (Step S5204). Standard deviation $\sigma_{df}$ of the peak frequency differences of water peaks and NAA peaks can be calculated from the standard deviation $\sigma_{W1}$ of the resonant frequencies $\nu_W$ of the water peaks, and the standard deviation $\sigma_{NAA1}$ of the resonant frequencies $\nu_{NAA}$ of the NAA peaks in accordance with the equation (10).

[Equation 10]

$$\sigma_{df} = \sqrt{\sigma_{W1}^2 + \sigma_{NAA1}^2} \quad (10)$$

Then, from the calculated standard deviation $\sigma_{df}$ of the peak frequency differences, temperature accuracy information (standard deviation) is calculated (Step S5205). The standard deviation $\sigma_T$ of the calculated temperatures can be calculated by converting $\sigma_{df}$ into temperature by using, for example, the temperature conversion equation described in Non-patent document 2. Specifically, the absolute value |p| of the coefficient p in the aforementioned equation (2) is multiplied with the standard deviation $\sigma_{df}$ of the peak frequency differences to obtain the standard deviation $\sigma_T$ of the calculated temperatures.

By the above procedure, there can be calculated the temperature accuracy information (standard deviation in the above case) of the temperatures calculated from the spectral information of water and the spectral information of NAA obtained by the measurement in an analytical manner.

As described above, the temperature accuracy information calculator 250 may be provided with a model function calculation means (model function calculator) for calculating model functions representing the two of calculated spectral peaks, a frequency accuracy calculation means (frequency accuracy calculator) for calculating accuracy information of the resonant frequencies of the two kinds of substances on the basis of the model functions, and a frequency difference accuracy calculation means (frequency difference accuracy calculator) for calculating accuracy information of the resonant frequency difference of the two kinds of substances from the accuracy information of the two of resonant frequencies, and the temperature accuracy information calculator 250 calculate the temperature accuracy information from the accuracy information of the resonant frequency difference.

In addition, also in this modified example, the temperature accuracy information to be calculated may be another statistic value such as dispersion and standard error.

Further, although the display information generator 260 generates the temperature table, the temperature image, and the temperature difference image as the display information in the above explanation of this embodiment, the display information to be generated is not limited to these. For example, a temperature image or temperature difference image of an arbitrary spatial resolution may be generated as the display information by interpolation or the like.

That is, the display information generator 260 may generate a temperature image of high resolution as the display information by interpolating the temperature information of the voxels. For example, a temperature image of higher resolution compared with the original temperature image is created by obtaining temperature information of new middle voxels through interpolation of the temperature information of the adjacent objective voxels.

Figure 11:
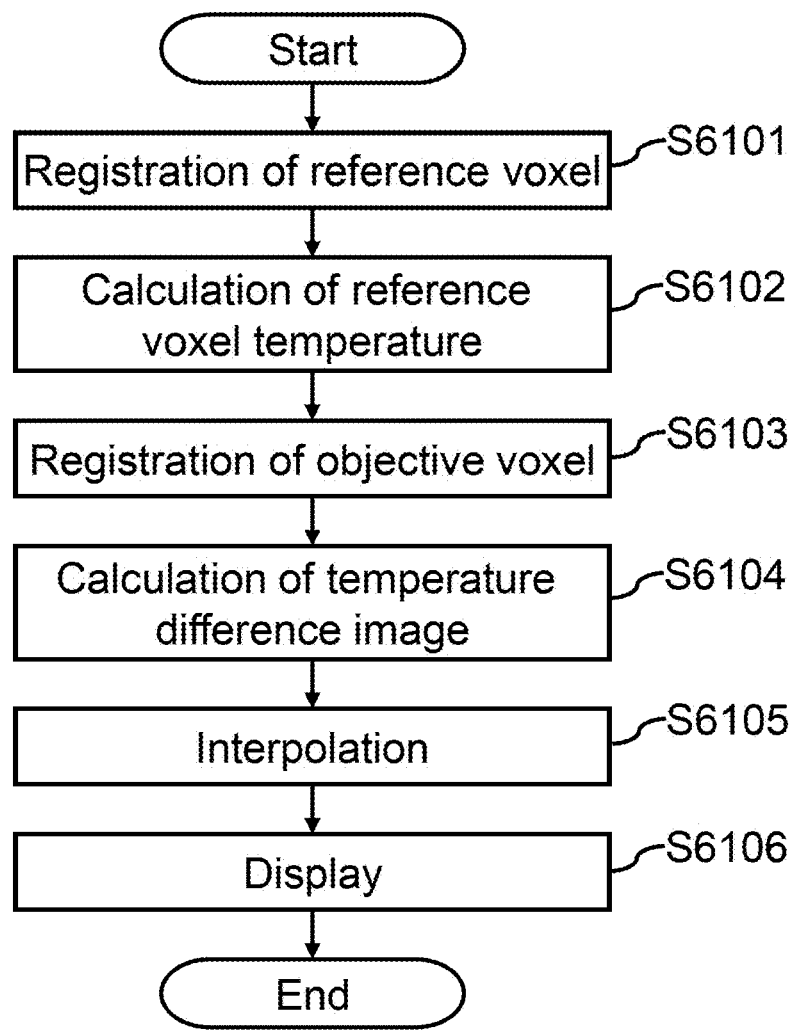
FIG. 11 is a flowchart of high resolution temperature difference image generation processing according to an embodiment of the present invention.

Further, the temperature difference image of higher resolution compared with the original temperature difference image (high resolution temperature difference image) is created by the following procedure. The flow of the processing that generates a temperature difference image of higher resolution compared with the original temperature difference image (high resolution temperature difference image) by interpolation performed by the display information generator 260 will be explained below with reference to the flowchart of FIG. 11.

First, a voxel serving as the reference selected from the matrix (voxels) of the temperature image obtained from the results measured with the MRSI sequence 300 by the above-mentioned method (henceforth referred to as image of low resolution) is received and registered (Step S6101). A plurality of voxels may be chosen as the reference.

Then, temperature of the reference voxel is calculated (Step S6102). When one voxel is chosen as the reference voxel, temperature of the voxel is used as the temperature of the reference voxel. When a plurality of voxels are chosen as the reference voxel, average of the temperatures of the selected voxels is calculated as the temperature of the reference voxel. In addition, when a plurality of voxels are chosen as the reference voxel, after sum of the water peaks and sum of the NAA peaks of the reference voxels are calculated, the resonant frequencies of water and NAA may be calculated by fitting, and the temperature may be calculated by using the conversion equation of the aforementioned equation (2) or the like.

Then, selected voxels for which a temperature difference image is calculated (referred to as objective voxels in this explanation) are received and registered (Step S6103). It is sufficient that at least one objective voxel is chosen, and the voxels of the whole measurement region may be selected.

Then, differences of the temperatures of the voxels included in the objective voxels and the temperature of the reference voxel are calculated, and a temperature difference image is calculated (Step S6104).

Further, a high resolution temperature difference image is generated from the temperature difference image by interpolation (Step S6105). As the interpolation used in the above operation, besides the linear interpolation, other known methods such as cubic interpolation and spline interpolation may also be used.

Finally, the high resolution temperature difference image calculated in Step S6105 is displayed on the display device 110 (Step S6106).

That is, the display information generator 260 is provide with a reference voxel reception means (reference voxel information acceptor) for receiving a reference voxel serving as the reference selected from the voxels, and a temperature difference information calculation means (temperature difference information calculator) for calculating differences of the temperature information of the voxels and the temperature information of the reference voxel as the temperature difference information, and the display information generator 260 generates a temperature difference image of desired resolution as the display information by interpolating the temperature difference information of the voxels.

Figure 12:
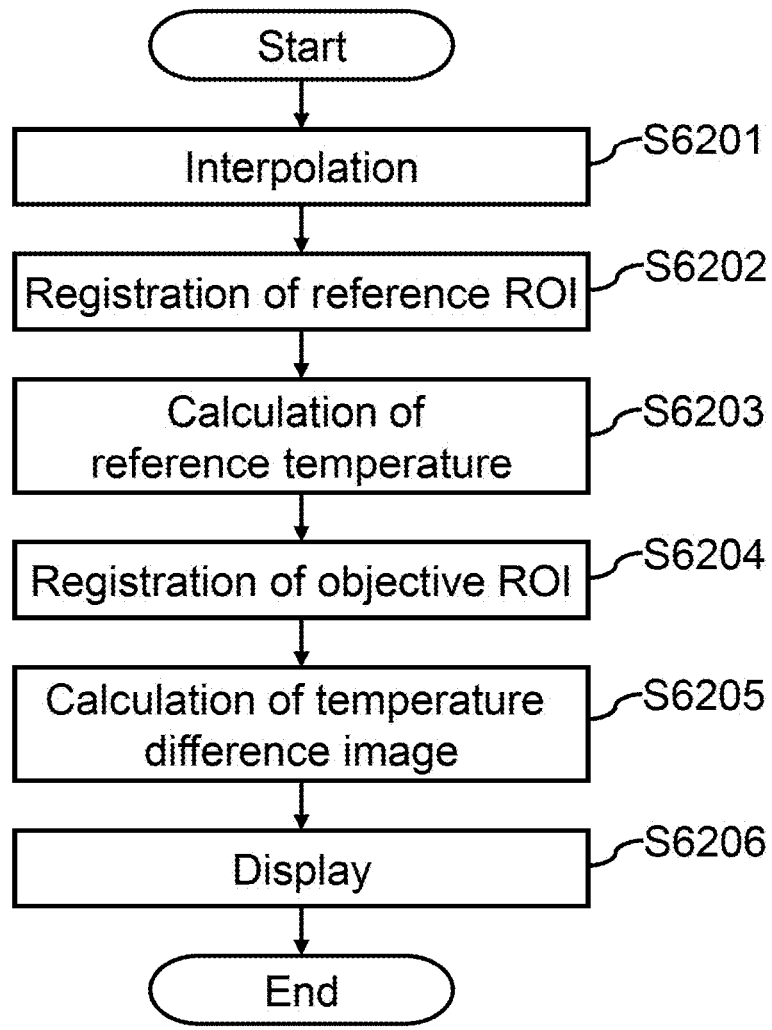
FIG. 12 is a flowchart of another example of high resolution temperature difference image generation processing according to an embodiment of the present invention.

However, the method for generating the high resolution temperature difference image is not limited to the method described above. A flow of a processing for generating a high resolution temperature difference image according to another method performed by the display information generator 260 is explained below with reference to the flowchart of FIG. 12.

First, a temperature image of high resolution is generated by interpolating a temperature image of low resolution obtained from the results measured with the MRSI sequence 300 (Step S6201). As the interpolation used in the above operation, besides the linear interpolation, other known methods such as cubic interpolation and spline interpolation may also be used.

Then, a selection of region of interest (ROI) serving as the reference on the high resolution temperature image obtained by the interpolation is received and registered (Step S6202). Two or more voxels may be included in the selected reference ROI. Further, the reference ROI may have an arbitrary shape such as circular, elliptic, or rectangular shape.

Then, temperature in the reference ROI (reference temperature) is calculated (Step S6203). In this example, the temperature information of the voxels included in the region selected as the reference ROI is used as the reference temperature. When a plurality of voxels are chosen as the reference voxel, average of the temperatures of the selected voxels is calculated as the reference temperature.

Then, a selected ROI for which a temperature difference image is calculated on the high resolution temperature image (referred to as objective ROI in this explanation) is received and registered (Step S6204). It is sufficient that at least one objective ROI is selected. Further, the whole measurement region may be selected as the objective ROI.

Then, differences of the temperatures of the voxels included in the objective ROI and the reference temperature are calculated, and a high resolution temperature difference image of which pixel values correspond to the results of the calculation is calculated (Step S6205).

Finally, the high resolution temperature difference image calculated in Step S6205 is displayed on the display device 110 (Step S6206).

That is, the display information generator 260 is provided with an interpolation means (interpolator) for generating a temperature image of desired resolution by interpolating the temperature information of the voxels, a reference region of interest reception means (reference region of interest information acceptor) for receiving a selected region of interest serving as the reference on the temperature image of the desired resolution, a reference temperature information calculation means (reference temperature information calculator) for calculating temperature information of the voxels in the region of interest serving the reference as the reference temperature information, and a temperature difference information calculation means (temperature difference information calculator) for calculating differences of the temperature information of the voxels of the temperature image of the desired resolution and the reference temperature information as the temperature difference information, and the display information generator 260 generates a temperature difference image of which pixel values correspond to the temperature difference information of the voxels as the display information.

A flow of a processing for calculating the high resolution temperature difference image based on a further procedure different from the above procedures is explained with reference to the flowchart of FIG. 13.

First, by spatially interpolating the spectral data of water and NAA obtained from the results of the measurement performed by using the MRSI sequence 300, spectral data of water and NAA of high resolution are calculated, respectively (Step S6301). As the interpolation used in the above operation, besides the linear interpolation, other known methods such as cubic interpolation and spline interpolation may also be used.

Then, temperature information is calculated from the spectrum data of water and NAA of high resolution according to the aforementioned method of this embodiment, and a temperature image of high resolution (high resolution temperature image) is generated (Step S6302). The display information generator 260 may make the temperature information calculator 240 perform the calculation of the temperature information calculation processing.

Then, a selected region of interest (ROI) serving as the reference on the high resolution temperature image (reference ROI) is received and registered (Step S6303). Two or more voxels may be included in the reference ROI. Further, the reference ROI may have an arbitrary shape such as circular, elliptic, or rectangular shape.

Then, temperature in the reference ROI (reference temperature) is calculated (Step S6304). In this example, the temperature information of the voxels included in the region selected as the reference ROI is used as the reference temperature. When a plurality of voxels are chosen as the reference voxel, average of the temperatures of the selected voxels is calculated as the reference temperature.

Then, a selection of ROI for which a temperature difference image is calculated on the high resolution temperature image (referred to as objective ROI in this explanation) is received and registered (Step S6305). It is sufficient that at least one objective ROI is selected. Further, the whole measurement region may be selected as the objective ROI.

Then, differences of the temperatures of the voxels included in the objective ROI and the reference temperature are calculated, and a high resolution temperature difference image of which pixel values correspond to the results of the calculation is calculated (Step S6306).

Finally, the high resolution temperature difference image calculated in Step S6306 is displayed on the display device 110 (Step S6307).

That is, the display information generator 260 is provided with an interpolation means (interpolator) for spatially interpolating the spectra of the voxels measured with the aforementioned sequence to obtain spectral data of desired resolution, a temperature image generation means (temperature image generator) for calculating temperature information of the interpolated voxels from the spectral data obtained by the interpolation and generating a temperature image of the aforementioned resolution of which pixel values correspond to the calculated temperature information, a reference region of interest reception means (reference region of interest information acceptor) for receiving a selected region of interest serving as the reference on the temperature image of the aforementioned resolution, a reference temperature information calculation means (reference temperature information calculator) for calculating the temperature information of the interpolated voxels in the region of interest serving as the reference as the reference temperature information, and a temperature difference information calculation means (temperature difference information calculator) for calculating differences of the temperature information of the interpolated voxels in the temperature image of the desired resolution and the reference temperature information as the temperature difference information, and the display information generator 260 generates a temperature difference image of which pixel values correspond to the temperature difference information of the interpolated voxels as the display information.

When a temperature image of high resolution is calculated by this procedure, an ROI (objective ROI) for which a temperature image is calculated is chosen on the high resolution temperature image generated in Step S6302 mentioned above, and the temperatures of the voxels included in the objective ROI are used as the pixel values of the pixels of the high resolution temperature image.

That is, the display information generator 260 is provided with an interpolation means (interpolator) for spatially interpolating the spectra of the voxels measured with the aforementioned sequence to obtain spectral data of desired resolution, calculates temperature information of the interpolated voxels from the spectral data obtained by the interpolation, and generates a temperature image of the aforementioned resolution of which pixel values correspond to the calculated temperature information as the display information.

In addition, when the display information generator 260 performs the interpolation processing, the display information to be displayed on the display device 110 may contain a switch 520 configured to select whether the interpolation processing is executed or not executed. When this switch 520 is pushed, the display information generator 260 executes the interpolation processing.

The temperature accuracy information obtained by the method of this embodiment may be used for determining the measurement parameters. For example, a plurality of MR images are obtained beforehand for one subject 101 with changing measurement parameters. Then, a plurality of kinds of temperature accuracy information are obtained with the aforementioned method by using a plurality of the obtained MR images. The plurality of kinds of the obtained temperature accuracy information are matched with the measurement parameters and stored in the storage device. Further, at the time of the measurement, measurement parameters such as measurement time giving the best temperature accuracy under the constraint conditions are adopted.

In the above method, for example, temperature accuracy information may be calculated for each of VOIs of various sizes and various positions in one MR image, and the temperature accuracy information may also be matched with the positions and stored. Furthermore, the temperature accuracy information may be matched with a histogram of pixel values of the voxels constituting the VOI for which the temperature accuracy information is calculated, not with the measurement parameters or measurement positions, and stored.

Although there is exemplified a case of using an MRSI sequence as the pulse sequence used in the non-water-suppressing measurement and water-suppressing measurement in the above explanation of this embodiment, the pulse sequence used in the non-water-suppressing measurement and water-suppressing measurement is not limited to that sequence. Any pulse sequence providing a spectrum of an objective substance of the measurement for each voxel can be used. For example, the sequence may be a sequence for a single region as the measurement object, which is called a pulse sequence for magnetic resonance spectroscopy (MRS sequence), a high-speed MRSI sequence using oscillating gradient magnetic fields, which is called echo planar spectroscopic imaging sequence (EPSI sequence), or the like.

DENOTATION OF REFERENCE NUMERALS

100: MRI device, 101: subject, 102: static magnetic field coil, 103: gradient coil, 104: shim coil, 105: transmission coil, 106: reception coil, 107: transmitter, 108: receiver, 109: computer, 110: display device, 111: external storage device, 112: power supply for gradient magnetic field, 113: power supply for shim, 114: sequence control device, 115: input device, 116: display screen, 120: MRI apparatus, 130: MRI apparatus, 210: scan controller, 220: arithmetic unit, 230: spectrum calculator, 240: temperature information calculator, 250: temperature accuracy information calculator, 260: display information generator, 300: MRSI sequence, 401: section, 402: section, 403: section, 404: voxel, 410: transverse image, 420: sagittal image, 430: coronal image, 501: temperature table, 502: temperature image, 520: switch, 511: temperature accuracy table, 512: temperature accuracy image

The invention claimed is:

1. A magnetic resonance imaging apparatus comprising:
a static magnetic field generator configured to generate a static magnetic field in a space in which a subject is placed;
a radio frequency magnetic field irradiator configured to irradiate a radio frequency magnetic field on the subject;
a gradient magnetic field applicator configured to apply a gradient magnetic field to the subject;
a detector configured to detect magnetic resonance signals generated from the subject;
a scan controller configured to obtain magnetic resonance signals of two kinds of substances showing difference of resonant frequencies by controlling operations of the gradient magnetic field applicator, the radio frequency magnetic field irradiator, and the detector;
an arithmetic unit configured to carry out operational processing of the magnetic resonance signals; and
a display device configured to display information obtained by the operational processing,
wherein the arithmetic unit comprises:
a spectrum calculator configured to calculate spectra of magnetic resonance signals of the two kinds of substances showing a difference of resonant frequencies,
a temperature information calculator configured to calculate temperature information for inside of the subject on the basis of peaks of the calculated spectra,
a temperature accuracy information calculator configured to calculate temperature accuracy information indicating accuracy of the temperature information on the basis of peaks of the calculated spectra, and
a display information generator configured to generate display information to be displayed on the display device on the basis of the temperature information and the temperature accuracy information, wherein the display information generator comprises an interpolator configured to spatially interpolate the spectra of a plurality of voxels measured with the sequence to obtain spectral data of desired resolution.

2. The magnetic resonance imaging apparatus according to claim 1, wherein the temperature information calculator comprises:
a resonant frequency calculator configured to determine functions representing the calculated spectral peaks, and calculate resonant frequencies of the two kinds of substances on the basis of the functions, and
a converter configured to convert difference of two of the calculated resonant frequencies into temperature information.

3. The magnetic resonance imaging apparatus according to claim 1,
wherein the temperature accuracy information calculator comprises:
a model function calculator configured to calculate model functions representing the calculated spectral peaks, respectively,
a virtual model function generator configured to generate a plurality of virtual model functions for each of the two kind of substances by adding a plurality of virtual noises to each of the model functions, and
a virtual temperature calculator configured to calculate virtual temperature from each of the virtual model functions, and
wherein the temperature accuracy information calculator subjects a plurality of the virtual temperatures to a statistical treatment to obtain the temperature accuracy information.

4. The magnetic resonance imaging apparatus according to claim 1,
wherein the temperature accuracy information calculator comprises:
a model function calculator configured to calculate model functions representing the calculated spectral peaks, respectively,
a frequency accuracy calculator configured to calculate accuracy information of the resonant frequencies of the two kinds of substances on the basis of the model functions, and
a frequency difference accuracy calculator configured to calculate accuracy information of the resonant frequency difference of the two kinds of substances from the accuracy information of the two of resonant frequencies, and
wherein the temperature accuracy information calculator calculates the temperature accuracy information from the accuracy information of the resonant frequency difference.

5. The magnetic resonance imaging apparatus according to claim 1, wherein the two of substances showing difference of resonant frequencies are water and a metabolite.

6. The magnetic resonance imaging apparatus according to claim 1, wherein the scan controller obtains magnetic resonance signals of the substances according to a magnetic resonance spectroscopy sequence.

7. The magnetic resonance imaging apparatus according to claim 1, wherein the scan controller obtains magnetic resonance signals of the substances according to one of a magnetic resonance spectroscopic imaging sequence and an echo planar spectroscopic imaging sequence.

8. The magnetic resonance imaging apparatus according to claim 7,
wherein the temperature information calculator calculates the temperature information for each of a plurality of voxels measured with the sequence, and
wherein the display information generator generates a temperature image of high resolution as the display information by interpolating the temperature information of the plurality of voxels.

9. The magnetic resonance imaging apparatus according to claim 7,
wherein the temperature information calculator calculates the temperature information for each of a plurality of voxels measured with the sequence,
wherein the display information generator comprises:
a reference voxel information acceptor configured to receive a selected reference voxel serving as a reference and selected from the plurality of voxels, and
a temperature difference information calculator configured to calculate differences of the temperature information of the plurality of voxels and the temperature information of the reference voxel as the temperature difference information, and
wherein the display information generator generates a temperature difference image of desired resolution as the display information by interpolating the temperature difference information of the plurality of voxels.

10. The magnetic resonance imaging apparatus according to claim 7,
wherein the temperature information calculator calculates the temperature information for each of a plurality of voxels measured with the sequence, and
wherein the display information generator comprises:
an interpolator configured to generate a temperature image of desired resolution by interpolating the temperature information of the plurality of voxels,
a reference region of interest information acceptor configured to receive a selected region of interest serving as the reference on the temperature image of the desired resolution,
a reference temperature information calculator configured to calculate temperature information of the plurality of voxels in the region of interest serving as the reference as the reference temperature information, and
a temperature difference information calculator configured to calculate differences of the temperature information of the plurality of voxels of the temperature image of the desired resolution and the reference temperature information as the temperature difference information, and
wherein the display information generator generates a temperature difference image of which pixel values correspond to the temperature difference information of the plurality of voxels as the display information.

11. The magnetic resonance imaging apparatus according to claim 7,
wherein the display information generator calculates temperature information of the interpolated plurality of voxels from the spectral data obtained by the interpolation, and generates a temperature image of the resolution of which pixel values correspond to the calculated temperature information as the display information.

12. The magnetic resonance imaging apparatus according to claim 7,
wherein the display information generator comprises:
a temperature image generator configured to calculate temperature information of the interpolated plurality of voxels from the spectral data obtained by the interpolation and generate a temperature image of the resolution of which pixel values correspond to the calculated temperature information,
a reference region of interest information acceptor configured to receive a selected region of interest serving as the reference on the temperature image of the resolution,
a reference temperature information calculator configured to calculate the temperature information of the interpolated plurality of voxels in the region of interest serving as the reference as the reference temperature information, and
a temperature difference information calculator configured to calculate differences of the temperature information of the interpolated plurality of voxels in the temperature image of the desired resolution and the reference temperature information as the temperature difference information, and
the display information generator generates a temperature difference image of which pixel values correspond to the temperature difference information of the interpolated plurality of voxels as the display information.

13. The magnetic resonance imaging apparatus according to claim 2, wherein the function is a Lorenz type function comprising resonant frequency as a variable.

14. The magnetic resonance imaging apparatus according to claim 3, wherein the temperature accuracy information is a standard deviation of the virtual temperatures.

15. A magnetic resonance imaging apparatus comprising:
a static magnetic field generator configured to generate a static magnetic field in a space in which a subject is placed;
a radio frequency magnetic field irradiator configured to irradiate a radio frequency magnetic field on the subject;
a gradient magnetic field applicator configured to apply a gradient magnetic field to the subject;
a detector configured to detect magnetic resonance signals generated from the subject;
a scan controller configured to obtain magnetic resonance signals of two kinds of substances showing difference of resonant frequencies by controlling operations of the gradient magnetic field applicator, the radio frequency magnetic field irradiator, and the detector;
an arithmetic unit configured to carry out operational processing of the magnetic resonance signals; and
a display device configured to display information obtained by the operational processing,
wherein the arithmetic unit comprises:
a spectrum calculator configured to calculate spectra of magnetic resonance signals of the two kinds of substances showing a difference of resonant frequencies,
a temperature information calculator configured to calculate temperature information for inside of the subject on the basis of peaks of the calculated spectra, a temperature accuracy information calculator configured to calculate temperature accuracy information indicating accuracy of the temperature information on the basis of peaks of the calculated spectra, wherein the temperature accuracy information calculator comprises:
- a model function calculator configured to calculate model functions representing the calculated spectral peaks, respectively,
- a virtual model function generator configured to generate a plurality of virtual model functions for each of the two kind of substances by adding a plurality of virtual noises to each of the model functions, and
- a virtual temperature calculator configured to calculate virtual temperature from each of the virtual model functions, and
wherein the temperature accuracy information calculator subjects a plurality of the virtual temperatures to a statistical treatment to obtain the temperature accuracy information, and
a display information generator configured to generate display information to be displayed on the display device on the basis of the temperature information and the temperature accuracy information.

* * * * *